(12) United States Patent  
Cheng et al.

(10) Patent No.: US 8,858,414 B2  
(45) Date of Patent: Oct. 14, 2014

(54) PROGRAMMABLE SEGMENTED VOLUMETRIC MODULATED ARC THERAPY FOR RESPIRATORY COORDINATION

(75) Inventors: Jason Chia-Hsien Cheng, Taipei (TW); Jian-Kuen Wu, Taipei (TW)

(73) Assignee: Jason Chia-Hsien Cheng, Taipei (TW)

( * ) Notice: Subject to any disclaimer, the term of this patent is extended or adjusted under 35 U.S.C. 154(b) by 159 days.

(21) Appl. No.: 13/364,014

(22) Filed: Feb. 1, 2012

(65) Prior Publication Data

US 2013/0193351 A1 Aug. 1, 2013

(51) Int. Cl.
*A61N 5/00* (2006.01)
*A61N 5/10* (2006.01)

(52) U.S. Cl.
USPC .................................. 600/1; 378/65

(58) Field of Classification Search
USPC ............... 600/1; 378/65; 250/492.1
See application file for complete search history.

(56) References Cited

U.S. PATENT DOCUMENTS

2010/0322381 A1* 12/2010 Stahl et al. ............. 378/65
2010/0329422 A1* 12/2010 Brown et al. ............ 378/65

OTHER PUBLICATIONS

Popescu et al. "Volumetric modulated arc therapy improves dosimetry and reduces treatment time compared to conventional intensity-modulated radiotherapy for locoregional radiotherapy of left-sided breast cancer and internal mammary nodes." Int. J. Radiation Oncology Bio. Phys., vol. 76, No. 1, pp. 287-295, 2010.*

McGrath et al., Volumetric modulated arc therapy for delivery of hypofractionated stereotactic lung radiotherapy: A dosimetric and treatment efficiency analysis, Radiotherapy and Oncology, 2010; 95:153-7.

Matuszak et al., Clinical applications of volumetric modulated arc therapy, Int. J. Radiation Oncology Biol. Phys., 2010, pp. 608-616, vol. 77, No. 2.

Court et al., Use of a realistic breathing lung phantom to evaluate dose delivery errors. Med Phys 2010, 37:5850-7.

Qian et al., Dose verification for respiratory-gated volumetric modulated arc therapy, Phys Med Biol., 2011, pp. 4827-4838, vol. 56.

Nicolini et al., Pre-clinical evaluation of respiratory-gated delivery of volumetric modulated arc therapy with RapidArc, Phys Med Biol., 2010, pp. N347-N357, vol. 55.

Chin et al., Investigation of a novel algorithm for true 4D-VMAT planning with comparison to tracked, gated and static delivery, Med Phys., 2011, pp. 2698-2707, vol. 38, No. 5.

Dobler et al., Commissioning of volumetric modulated arc therapy (VMAT) in a dual-vendor environment, Radiotherapy and Oncology, 2011, pp. 86-89, vol. 99.

Kida et al., rD-CBCT reconstruction using MV portal imaging during volumetric modulated arc therapy, Radiotherapy and Oncology, 2011, pp. 380-385, vol. 100.

(Continued)

*Primary Examiner* — Jacqueline Cheng
*Assistant Examiner* — Kaylee Wilson
(74) *Attorney, Agent, or Firm* — WPAT, P.C.; Anthony King; Kay Yang

(57) ABSTRACT

The invention designs the segmented short-arc VMAT plan, modified from the original long-arc VMAT, to fit the breath-hold interval. The modified VMAT of the invention has the advantages of its applicability to different planning systems for variously long arcs and its preprogrammed arc segmentation for summated dose consistency. Using segmented short-arc modification from the original long-arc VMAT plan is accurate for dose planning and delivery, as well as tolerable for breath-hold VMAT.

14 Claims, 3 Drawing Sheets
(1 of 3 Drawing Sheet(s) Filed in Color)

(56) References Cited

OTHER PUBLICATIONS

Ruben et al., The effect of intensity-modulated radiotherapy on addiation-induced second malignancies. Int. J. Radiation Oncology Biol. Phys., 2008, pp. 1530-1536, vol. 70, No. 5.

Hall et al., Intensity-modulated radiation herapy, protons, and the risk of second cancers, Int. J. Radiation Oncology Biol. Phys., 2006, pp. 1-7, vol. 65, No. 1.

Bertelsen et al., Single Arc Volumetric Modulated Arc Therapy of head and neck cancer, Radiotherapy and Oncology, 2010, pp. 142-148, vol. 95.

* cited by examiner

PROGRAMMABLE SEGMENTED VOLUMETRIC MODULATED ARC THERAPY FOR RESPIRATORY COORDINATION

FIELD OF THE INVENTION

The invention relates to a system and a method for volumetric modulated arc therapy (VMAT). In particular, the invention provides a system and a method for programmable segmented VMAT.

BACKGROUND OF THE INVENTION

Radiation therapy consists of the use of ionizing radiation to treat living tissue, usually tumors. There are many different types of ionizing radiation used in radiation therapy, including high energy x-rays, electron beams, and proton beams. However, the process of administering the radiation to a patient can be somewhat generalized regardless of the type of radiation used. According to conventional radiation therapy, a beam of radiation is directed toward a tumor located within a patient. The radiation beam delivers a predetermined dose of therapeutic radiation to the tumor according to a treatment plan. The delivered radiation kills cells of the tumor by causing ionizations within the cells. However, use of a single pre-treatment scan can lead to a large planning target margin and uncertainty in normal tissue dose due to patient variations, such as organ movement, shrinkage and deformation, which can occur from the start of a treatment session to the end of the treatment session.

The radiation therapy techniques include the use of Intensity Modulated Radiotherapy ("IMRT"), typically by means of a radiotherapy system, such as a linear accelerator, equipped with a multileaf collimator ("MLC"). Use of multileaf collimators in general, and IMRT in particular, allows the radiologist to treat a patient from multiple angles while varying the shape and dose of the radiation beam, thereby providing greatly enhanced ability to deliver radiation to a target within a treatment volume while avoiding excess irradiation of nearby healthy tissue. The recently developed and clinically adopted technique known as volumetric modulated arc therapy (VMAT) improves target conformity and organ sparing by use of rotational intensity modulated radiation therapy (IMRT) and more control points (gantry locations) for intensity optimization (McGrath S D, Matuszak M M, Yan D, Kestin L L, Martinez A A, Grills I. *Volumetric modulated arc therapy for delivery of hypofractionated stereotactic lung radiotherapy: A dosimetric and treatment efficiency analysis. Radiother Oncol* 2010; 95:153-7; Matuszak M M, Yan D, Grills I, Martinez A. *Clinical applications of volumetric modulated arc therapy. Int J Radiat Oncol Biol Phys* 2010; 77:608-16). VMAT is a new type of intensity-modulated radiation therapy (IMRT) treatment technique that uses the same hardware (i.e. a digital linear accelerator) as used for IMRT or conformal treatment, but delivers the radiotherapy treatment using rotational or arc geometry rather than several static beams. This technique uses continuous modulation (i.e. moving the collimator leaves) of the multileaf collimator (MLC) fields, continuous change of the fluence rate (the intensity of the X rays) and gantry rotation speed across a single or multiple 360 degree rotation(s). This significantly reduces beam delivery time compared to conventional fixed field IMRT (otherwise known as step and shoot IMRT). During a VMAT treatment, the Linear Accelerator rotates around the patient while the radiation beam is shaped and reshaped as it is continuously delivered from virtually every angle in a revolution. During a VMAT treatment, specialized software algorithms will vary the three parameters simultaneously: the speed of rotation around the patient, the shape of the MLC aperture, and the dose delivery rate. The target volume dose does not change when using VMAT. The amount of scatter and leakage radiation dose to the rest of the body is reduced compared to conventional IMRT. Varian (Varian Medical Systems, Palo Alto, Calif., USA) develops a VMAT product marketed as RapidArc. The US FDA approved RapidArc for clinical use in February 2008. In its first released software version, only one or two full rotation arcs could be planned. In the second software upgrade (Aria version 8.6) released in the first half of 2009, partial arcs, arcs with exclusion zones (e.g. so that the entry angle through a metallic hip replacement can be avoided) and arcs from different gantry angles (e.g. vertex fields for cranial treatments) allowed greater freedoms of dose intensity modulation for complex target volumes where adjacent critical normal tissue structures need to be avoided.

Elekta (Elekta AB, Stockholm, Sweden) also have a product named VMAT, which does not use Otto's algorithm, but uses a proprietary algorithm. This emphasized multiple arcs from the earliest software releases, in contrast to the early Varian releases. The planning technique for VMAT has evolved with software upgrades. When first introduced, a plan using a double arc to treat a 2 Gray planning target volume (PTV), the first arc optimization is dosed to 1 Gray. The second arc is then optimized to the existing single arc plan, with the smoothing and filling of cold spots and the cooling of hot spots, leading to a more homogenous PTV dosing. With the latest software versions, the planner defines two arcs with starting and stopping positions, and then the optimization occurs to the full 2Gy to the PTV. The VMAT optimization is a two-step process. A set of ideal intensity maps is generated first—this takes 10-20 minutes. A leaf sequencing process where leaves move smoothly between adjacent arc segments follows this. This process used to take 20 minutes but has now been substantially shortened by employing four quad processors to optimize four arc segments simultaneously. Additional boost volumes can be added with a second or third arc—allowing concomitant boosts or field in field effects. The additional arc may also provide supplementary aperture shape variation for a complex dose distribution.

U.S. Pat. No. 8,027,431 provides a system and method to receive a radiation treatment plan for delivering at least a portion of a prescribed radiation dose to a target volume in a series of individual treatment beams in an arc around the target volume, each individual treatment beam having a start angle and a stop angle; and deliver a portion of the prescribed radiation dose to the target volume over each of the segments, the segments arranged in a contiguous manner on the arc and the delivery of the prescribed radiation dose is continuous through the segments. However, there has not been a solution to breath-hold coordination for the dynamic delivery of the VMAT system (for example, Eleka VMAT, Elekta Oncology System Ltd., Crawley, West Sussex, UK).

The delivery of each arc of VMAT usually takes more than 1 to 2 minutes, longer than a single tolerable breath hold. Breath hold and respiratory gating are two established strategies for reducing respiration-induced organ motion in radiotherapy. Deep-inspiration breath hold is a controlled breathing technique in which the patient performs a supervised breath hold during radiotherapy, with the dual benefits of reduced respiratory motion from the breath hold and increased normal tissue sparing from the increased tissue volume. Respiratory gating depends on a device external to the patient monitoring breathing and allows delivery of radiation only during certain time intervals, synchronous with the patient's respiratory cycle. Gated radiotherapy requires less patient effort than breath hold, but has more organ motion than static breath hold. Respiration-induced dose-delivery errors are demonstrated with a realistic breathing lung phantom, with exceptionally significant errors by single-arc VMAT using a high dose rate (Court L E, Seco J, Lu X Q, Ebe K, Mayo C, Ionascu D et al. *Use of a realistic breathing lung phantom to evaluate dose delivery errors. Med Phys* 2010; 37:5850-7). Efforts have been made to develop gating solutions to VMAT delivery. Varian's TrueBeam™ (Varian Medical Systems, Palo Alto, Calif., USA) first supported gated VMAT by responding a gating signal from a real-time position management (RPM™) system. Qian et al. adapted a log-file-based dose reconstruction and verified the fidelity of gated VMAT delivery for three patients with lung or pancreatic tumors with three simulated respiratory periods (Qian J, Xing L, Liu W Luxton G. *Dose verification for respiratory-gated volumetric modulated arc therapy. Phys Med Biol* 2011; 56:4827-38). Preclinical evaluation of Varian's gated RapidArc delivery by use of 2-dimensional dose verification was satisfactorily conducted (Nicolini G, Vanetti E, Clivio A, Fogliata A, Cozzi L. *Pre-clinical evaluation of respiratory-gated delivery of volumetric modulated arc therapy with RapidArc. Phys Med Biol* 2010; 55:N347-57). All the work focuses on Varian's VMAT and RPM™ gating systems, which use the signal of chest wall movement to represent respiratory oscillation and involve complex interactions between MLC kinetics, dose-rate modulation, and gantry rotation. A 4-dimensional VMAT planning framework is under investigation, with the contributions of beams and organ motion from different breathing phases integrated into the optimization process. However, such a strategy is more theoretical than practical for fractionated treatment (Chin E, Otto K. *Investigation of a novel algorithm for true 4D-VMAT planning with comparison to tracked, gated and static delivery. Med Phys* 2011; 38:2698-707). Radiotherapy delivered by Elekta's linear accelerator has used the breath-hold strategy, either by active breathing coordination or passive abdominal compression, to reduce respiration-induced dose errors. Therefore, breath-hold timing and interval are more voluntary and predictable for gated VMAT. To deliver dynamic VMAT within the breath-hold intervals, segmented short arcs of less than 20 to 30 seconds each are required. The available treatment planning systems either have a minimum requirement of gantry rotation range for the arc design, such as ≥90° arc with the Pinnacle system, or have less satisfactory planning results with short arcs (Bertelsen A, Hansen C R, Johansen J, Brink C. *Single Arc Volumetric Modulated Arc Therapy of head and neck cancer. Radiother Oncol* 2010; 95:142-8). To our knowledge, there has not been any gating solution to VMAT delivery by Elekta's accelerator (Dobler B, Groeger C, Treutwein M et al. *Commissioning of volumetric modulated arc therapy (VMAT) in a dual-vendor environment. Radiother Oncol* 2011; 99:86-9; Kida S, Saotome N, Masutani Y et al. *4D-CBCT reconstruction using MV portal imaging during volumetric modulated arc therapy. Radiother Oncol* 2011; 100:380-5).

Therefore, there is still a need to find a solution to solve the problem in taking the time longer than a single tolerable breath hold to deliver each arc of VMAT.

SUMMARY OF THE INVENTION

The invention provides a system and a method for programmable segmented VMAT, modified from the original long-arc VMAT, to fit the breath-hold interval. One object of the invention is to provide a programmable method for setting subarcs in a segmented short-arc volumetric modulated arc therapy (VMAT), comprising dividing the arc in the VMAT into plural subarcs wherein each subarc is in an interval less than a single breath-hold.

Another object of the invention is to provide a system setting split short arcs in a programmably segmented short-arc volumetric modulated arc therapy (VMAT), comprising a unit dividing the arc in the VMAT into plural subarcs wherein each subarc is in an interval less than a single breath-hold.

BRIEF DESCRIPTION OF THE DRAWING

The patent or application file contains at least one drawing executed in color. Copies of this patent or patent application publication with color drawing(s) will be provided by the Office upon request and payment of the necessary fee.

FIG. 2 (B) shows the accurate 2-dimensional dose verification on coronal section for original long-arc VMAT and modified short-arc VMAT of a representative patient.

DETAILED DESCRIPTION OF THE INVENTION

Figure 1:
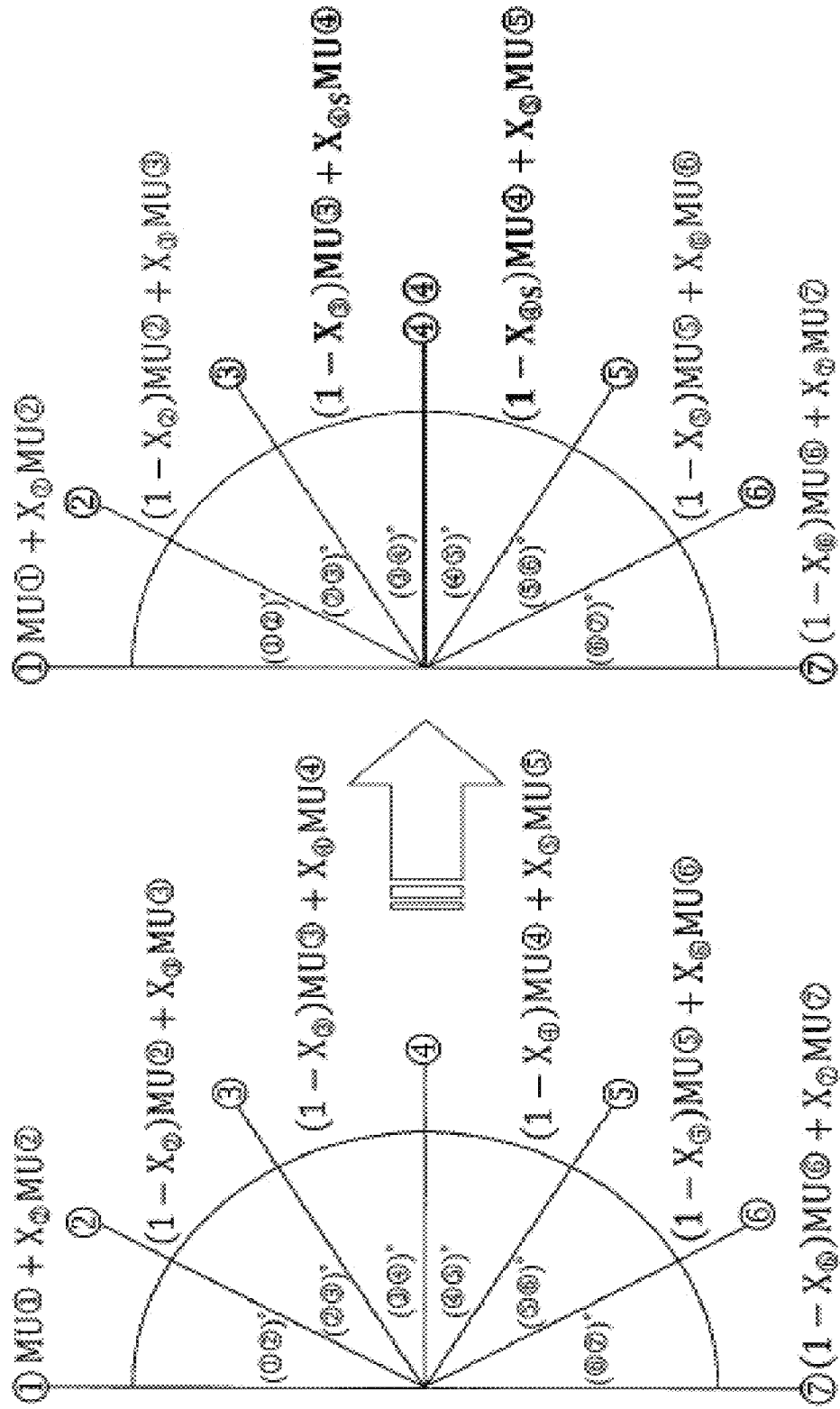
FIG. 1 shows an example for illustrating the algorithm used in the method and system of the invention.
Figure 2A:
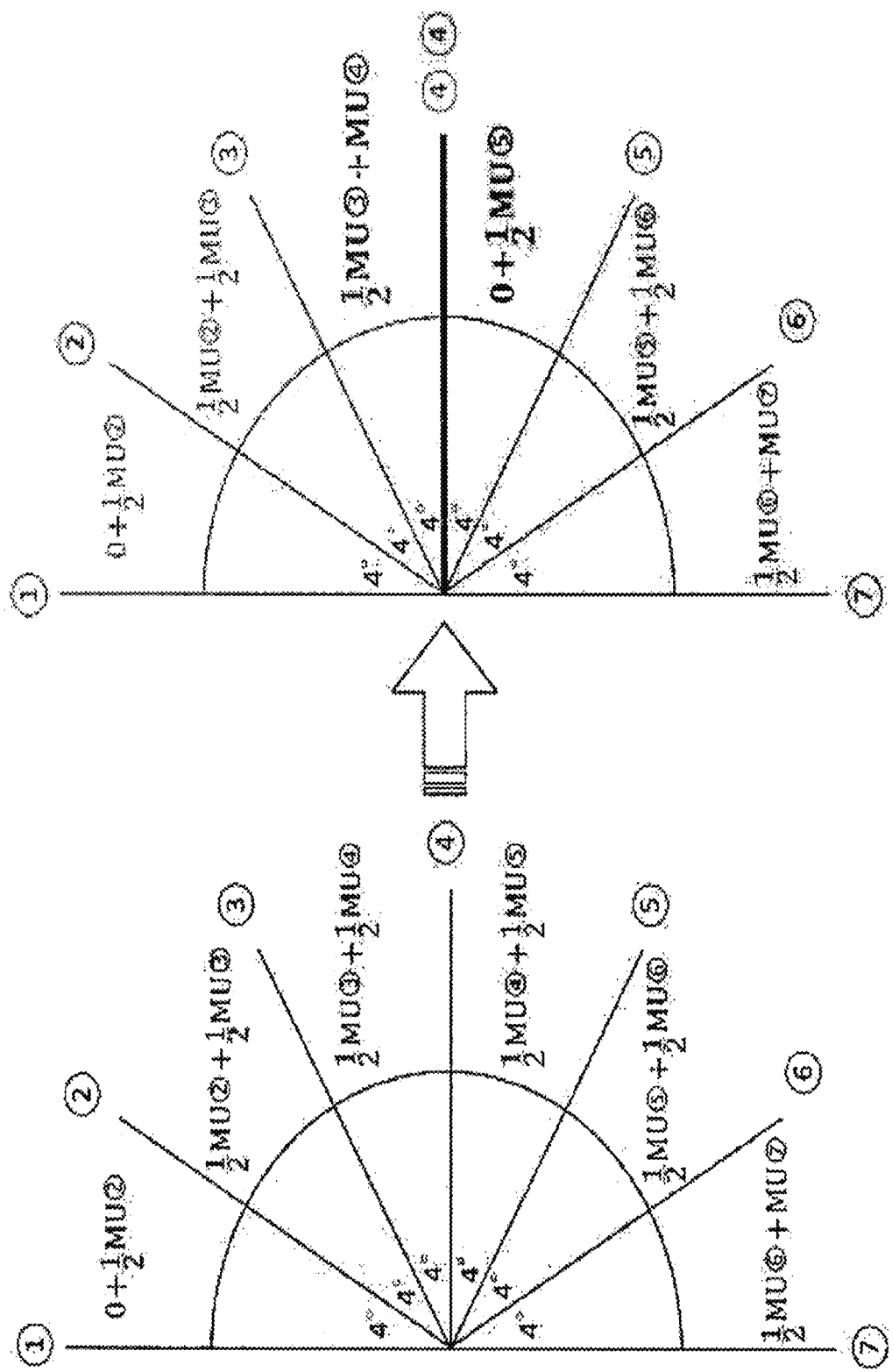
FIG. 2 (A) shows the simplified algorithm of modifying the original long-arc volumetric modulated arc therapy (VMAT) (black color) with the segmented short-arc VMAT (blue and red colors) for the split delivery for the system requiring the monitor unit (MU) of zero at the starting point of each arc.
Figure 2B:
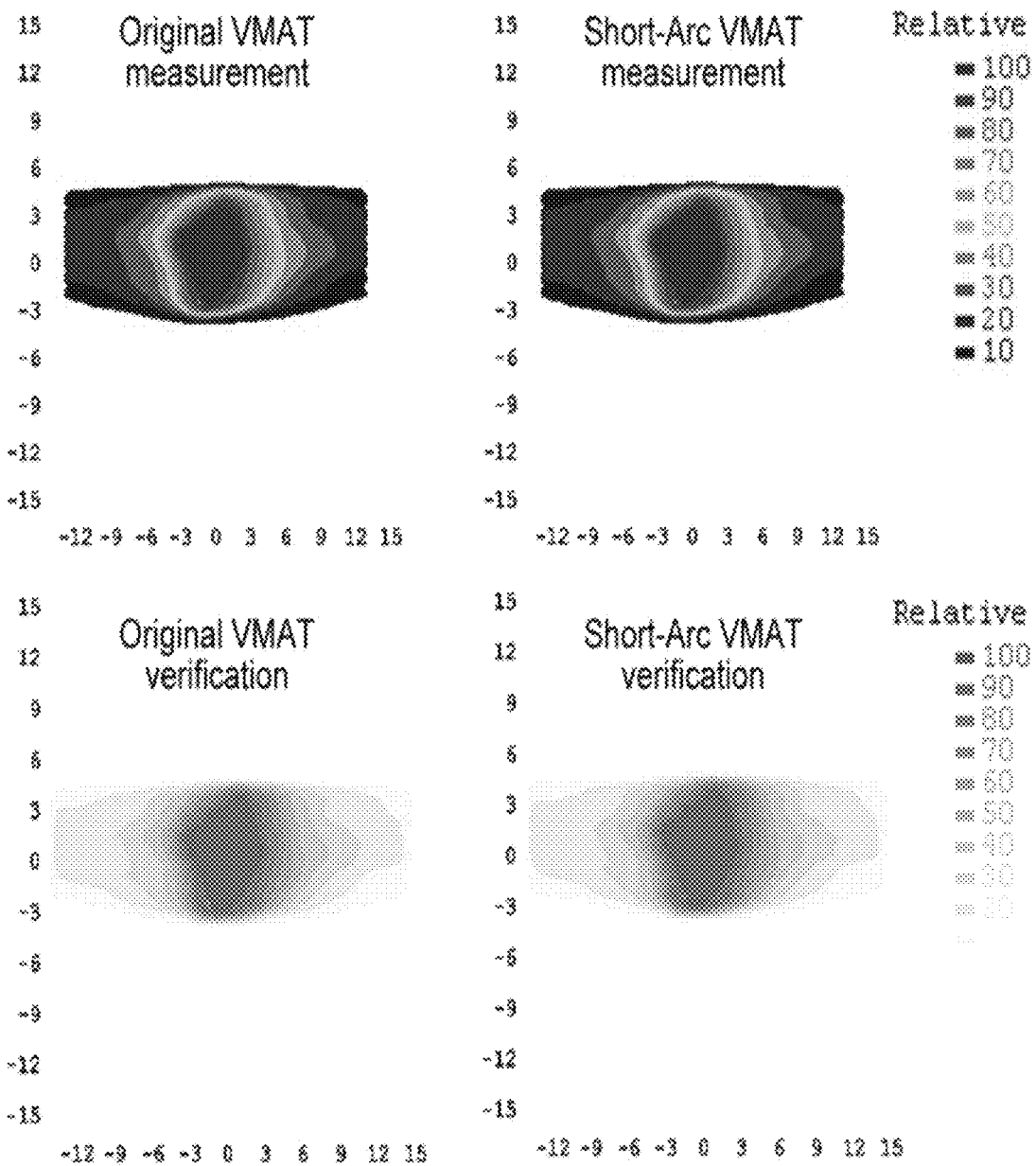

The following description is provided to enable a person skilled in the art to make and use the embodiments described herein and sets forth the best mode contemplated therefor. Various modifications, however, will remain readily apparent to those skilled in the art.

Clinically, linac-based radiotherapy uses VMAT with 1-2 arcs for delivering conformal dose distribution. VMAT produces conformal dose distribution by continuously rotating the gantry while modulating the aperture shape and weight. Fundamentally, VMAT is a special form of IMRT with a large number of incident beams, each having an aperture shape and intensity, subject to machine delivery constraints.

The invention provides a programmable segmented short-arc VMAT plan, modified from the original long-arc VMAT, designed to fit the breath-hold interval. The modified VMAT of the invention has the advantages of applicability to different planning systems for variously long arcs and preprogrammed arc segmentation for summated dose consistency. Segmented short-arc modification of the original long-arc VMAT plan allows accurate dose planning and delivery, as well as tolerability for breath-hold VMAT.

In one aspect, the invention provides a programmable method for setting subarcs in a segmented short-arc volumetric modulated arc therapy (VMAT), comprising dividing the arc in the VMAT into plural subarcs wherein each subarc is in an interval less than a single breath-hold. In one embodiment, each subarc is requires less than 40 seconds. Preferably, each subarc takes a time less than 30 seconds, more preferably, less than 20 or 15 seconds. In one embodiment, each subarc takes a time of about 15 to about 40 seconds, more preferably, about 15 to about 30 seconds or about 20 to about 30 seconds.

In one embodiment, the invention provides a programmable method for setting subarcs in a segmented short-arc volumetric modulated arc therapy (VMAT) to fit the breath-hold interval, comprising:

(a) dividing the arc in the VMAT into plural subarcs;
(b) setting four cut-edge control points within each subarc to form three segments, each segment defining a range over which a prescribed dose of radiation is delivered with the segments arranged in a continuous manner on the subarc and the delivery of the prescribed radiation dose being continuous through the segments;

(c) setting monitor points (MUs) for the segments within each subarc, wherein the monitor units for a starting (first) control point, second control point, third control point and stopping (fourth) control point are designated as $MU_1$, $MU_2$, $MU_3$ and $MU_4$, respectively, and the stopping control point is the starting point of the subsequent subarc; and (d) determining a dose distribution within each subarc by setting delivered MUs in each segment, wherein the delivered MUs in the first segment are distributed according to the formula: $MU_1+X_2MU_2$; the delivered MUs in the second segment are distributed according to the formula: $(1-X_2) MU_2+X_3MU_3$; and the delivered MUs in the third segment are distributed according to the formula: $(1-X_3) MU_3+X_{4s}MU_4$; $X_2$ is the proportion of the delivered MUs distributed for the segment between the starting control point and the second control point, while $(1-X_2)$ is the proportion of the delivered MUs distributed for the segment between the second control point and the third control point; $X_3$ is the proportion of the delivered MUs distributed for the segment between the second control point and the third control point, while $(1-X_3)$ is the proportion of the delivered MUs distributed for the segment between the third control point and the fourth (stopping) control point; and $X_{4s}$ is the proportion for converting the delivered MUs at the stopping control point to that at the starting control point of the subsequent subarc.

According to one embodiment of the invention, the $MU_1$ of the first (starting) segment is 0. According to another embodiment of the invention, $X_{4s}=1$.

In another aspect, the invention provides a system setting split short arcs in a programmably segmented short-arc volumetric modulated arc therapy (VMAT), comprising a unit dividing the arc in the VMAT into plural subarcs wherein each subarc is in an interval less than a single breath-hold. In one embodiment, each subarc requires less than 40 seconds; more preferably, less than 30 seconds, more preferably, less than 20 or 15 seconds. In one embodiment, each subarc takes a time of about 15 to about 40 seconds, more preferably, about 15 to about 30 seconds or about 20 to about 30 seconds.

In another embodiment, the invention provides a system setting split short arcs in a segmented short-arc volumetric modulated arc therapy (VMAT), comprising a unit for dividing the arc in the VMAT to subarcs; a unit for setting four cut-edge control points within each subarc to form three segments, each segment defining a range over which a prescribed dose of radiation is delivered with the segments arranged in a continuous manner on the subarc and the delivery of the prescribed radiation dose being continuous through the segments; a unit for setting monitor points (MUs) for the segments within each subarc, wherein the MUs for a starting (first) control point, second control point, third control point and stopping (fourth) control point are designated as $MU_1$, $MU_2$, $MU_3$ and $MU_4$, respectively, and the stopping control point is the starting point of the subsequent subarc; and a unit for determining a dose distribution within each subarc by setting delivered MUs in each segment, wherein the delivered MUs in the first segment are distributed according to the formula: $MU_1+X_2MU_2$; the delivered MUs in the second segment are distributed according to the formula: $(1-X_2) MU_2+X_3MU_3$; and the delivered MUs in the third segment are distributed according to the formula: $(1-X_3)MU_3+X_{4s}MU_4$, $X_2$ is the proportion of the delivered MUs distributed for the segment between the starting control point and the second control point, while $(1-X_2)$ is the proportion of the delivered MUs distributed for the segment between the second control point and the third control point;

$X_3$ is the proportion of the delivered MUs distributed for the segment between the second control point and the third control point, while $(1-X_3)$ is the proportion of the delivered MUs distributed for the segment between the third control point and the fourth (stopping) control point; and $X_{4s}$ is the proportion for converting the delivered MUs at the stopping control point to that at the starting control point of the subsequent subarc.

According to the invention, the long arc used in VMAT known in the art is divided into split short subarcs, each taking a time less than that needed for a breath-hold for respiratory coordination. The known VMAT plans with either full arcs or partial arcs take longer than one breath hold for delivery of radiation. The invention modifies the VMAT plans by using split short arcs of less than 30 seconds each. Preferably, each subarc takes a time less than 40 seconds; more preferably, less than 30 seconds, more preferably, less than 20 or 15 seconds. In one embodiment, each subarc takes a time of about 15 to about 40 seconds, more preferably, about 15 to about 30 seconds or about 20 to about 30 seconds.

According to the invention, the prescribed radiation dose is delivered over each of the segments. It is noted that the segments are arranged in a contiguous manner in the subarc around the patient and the delivery of the prescribed radiation dose is continuous through the segments. According to the invention, the radiation dose may be delivered in short strobes (or bursts) of high intensity radiation (e.g., the maximum available dose rate) such that deviation from the original plan caused by continuous gantry motion is minimized.

According to the invention, within each subarc, cut-edge control points are set to form segments. Each segment defines a range over which a prescribed dose of radiation is delivered, and the segments are arranged in a continuous manner on the subarc. The delivery of the prescribed radiation dose is continuous through the segments. The end gantry angle of each short arc is the starting gantry angle of the next short arc.

According to the invention, the monitor units (MUs) of arcs are reassigned between the short arcs. The beam of radiotherapy is delivered by a certain number of machine monitor units (MUs), a measure of machine radiation output. MUs are important as second cancer risk in patients treated with radiotherapy is proportional to how many MUs are needed per treatment course (Hall E J: *Intensity-modulated radiation therapy, protons, and the risk of second cancers, Int J Radiat Oncol Biol Phys* 2006, 65(1):1-7; Ruben J D, Davis S, Evans C, Jones P, Gagliardi F, Haynes M, Hunter A: *The effect of intensity-modulated radiotherapy on radiation-induced second malignancies. Int J Radiat Oncol Biol Phys* 2008, 70(5): 1530-6).

In the case of a known VMAT arc coming from sequenced static fields, the MUs of the control points between two adjacent segments of arc are considered as half-weighted, while the MUs of the control points at the edge are considered full value. In a preferred embodiment of the invention, the half-MUs of the control point at the edge between the split short arcs (i.e., subarc) are added from the next subarc to the previous subarc, because in this case zero MU is required for the beginning control point of the subarc. According to the invention, the VMAT plans involve modification of the number of control points, MU weight at each control point, and starting and end gantry angles.

According to the invention, a dose distribution within each subarc is determined by setting delivered MUs in each segment, wherein the delivered MUs in the first segment are distributed according to the formula: $MU_1+X_2MU_2$; the delivered MUs in the second segment are distributed according to the formula: $(1-X_2)MU_2+X_3MU_3$; and the delivered MUs in the third segment are distributed according to the formula: $(1-X_3)MU_3+X_{4s}MU_4$; $X_2$ is the proportion of the delivered MUs distributed for the segment between the starting control point and the second control point, while $(1-X_2)$ is the proportion of the delivered MUs distributed for the segment between the second control point and the third control point; $X_3$ is the proportion of the delivered MUs distributed for the segment between the second control point and the third control point, while $(1-X_3)$ is the proportion of the delivered MUs distributed for the segment between the third control point and the stopping control point; and $X_{4s}$ is the proportion for converting the delivered MUs at the stopping control point to that at the starting control point of the subsequent subarc.

According to the invention, the $MU_1$ of the first (starting) segment is determined depending on the initial settings of the VMAT. In some VMAT systems, the $MU_1$ of the first (starting) segment is set as 0, while in other systems, the MU1 is not necessarily 0. According to another embodiment of the invention, $X_{4s}=1$.

The schematic illustration shown in FIG. 1 is a preferred example illustrating the method and system of the VMAT, wherein the left plot shows an example of the delivered MUs in a VMAT known in the art, whereas the right plot shows an example of the invention. In the left plot, seven control points are set and the MUs are evenly and continuously delivered with six segments in a longer arc. However, in the right plot, one arc with the stopping point at the seventh control point is divided into two subarcs with the stopping points at the fourth control point and the seventh control point. Particularly, two subarcs, the starting subarc and the subsequent subarc, are illustrated, but the other subarcs are not shown. In the scheme, MU① represents the monitor units (MUs) designed by the treatment planning system for control point ②; ①; MU② represents the MUs designed by the treatment planning system for control point ②; MU③ represents the monitor units (MUs) designed by the treatment planning system for control point ③; MU④ represents the monitor units (MUs) designed by the treatment planning system for control point ④; MU⑤ represents the monitor units (MUs) designed by the treatment planning system for control point ⑤; MU⑥ represents the monitor units (MUs) designed by the treatment planning system for control point ⑥; and MU⑦ represents the monitor units (MUs) designed by the treatment planning system for control point ⑦. $X_{②}$ represents the proportion of delivered MUs distributed for the arc between control points ① and ②, while $(1-X_{②})$ represents the proportion of delivered MUs distributed for the arc between control points ② and ③. $X_{③}$ represents the proportion of delivered MUs distributed for the arc between control points ② and ③, while $(1-X_{③})$ represents the proportion of delivered MUs distributed for the arc between control points ③ and ④. $X_{④s}$ represents the proportion for converting the delivered MUs at the stopping control point to that at the starting control point of the subsequent subarc, while $(1-X_{④s})$ represents the proportion of delivered MUs distributed for the arc between control points ④ and ⑤. $X_{⑤}$ represents the proportion of delivered MUs distributed for the arc between control points ④ and ⑤, while $(1-X_{⑤})$ represents the proportion of delivered MUs distributed for the arc between control points ⑤ and ⑥. $X_{⑥}$ represents the proportion of delivered MUs distributed for the arc between control points ⑤ and ⑥, while $(1-X_{⑥})$ represents the proportion of delivered MUs distributed for the arc between control points ⑥ and ⑦.

Referring to FIG. 1, control point ① represents the starting control point and the formula between two control points shows weighted MU value for distribution within each segment. The starting subarc includes 4 control points, ①, ②, ③ and ④ and the last control point ④ represents the starting point of the subsequent subarc that includes control points, ④, ⑤, ⑥ and ⑦. (Ⓝ, Ⓝ)° shows the angle between control points Ⓝ and Ⓝ; for example, (①, ②)° represents the angle between control points ① and ②.

In some embodiments, the radiation treatment plan is provided to a radiation therapy treatment delivery system embodied in a computer or processor readable medium such as a file or series of files embodied in a memory storage unit. The system of the invention may be implemented as an optical disk, a CD-ROM, RAM, a flash ROM, or any type of memory storage unit now known or that becomes known in the future.

The method and system of the invention provide individualized treatment planning modification for VMAT and propose a solution of dividing the long arc from the original VMAT plan into split short arcs, with each short-arc delivery taking less than 30 seconds. The method and system can be incorporated into any conventional VMAT plan to solve the problem of conventional VMAT plans lacking coordination of VMAT and breath-hold interval.

Those in the art will appreciate that various adaptations and modifications of the above-described embodiments can be configured without departing from the scope and spirit of the claims. Therefore, it is to be understood that the claims may be practiced other than as specifically described herein.

EXAMPLE

Example 1

VMAT Plan Modification

Five pancreatic cancer patients whose VMAT plans were originally designed by the SmartArc module version 9.0 of the Pinnacle planning system (Qian J, Xing L, Liu W, Luxton G. *Dose verification for respiratory-gated volumetric modulated arc therapy. Phys Med Biol* 2011; 56:4827-38) were included in this study. The original VMAT plans with either full arcs or partial arcs taking longer than one breath hold for delivery were modified to use split short arcs of less than 30 seconds each. Because the original VMAT designs used the relatively constant gantry rate (1-5 degrees/second), the cut-edge control points of split short arcs were selected every 30-50 degrees. The end gantry angle of each short arc was the starting gantry angle of the next short arc. The monitor units (MUs) of arcs in the RTP files of the record-and-verify system, MOSAIQ version 1.6 (IMPAC Medical Systems, Inc, Sunnyvale, Calif., USA), were reassigned between the short arcs. In the case of an original VMAT arc coming from sequenced static fields, the MUs of the control points between two adjacent segments of arc are considered as half-weighted, while the MUs of the control points at the edge are considered for their whole value. The originally designed half-MUs of the control point at the edge between the split short arcs were added from the next short arc to the previous short arc, because zero MU is required for the beginning control point of the arc by the Pinnacle3 planning system. The algorithm of the split-arc modification is shown in FIG. 1A. The program of the RTP file in the record-and-verify system for each short-arc VMAT delivery was modified with the revised number of control points, MU weight at each control point, as well as the starting and end gantry angles.

The dose grid resolution was 0.4 cm for inverse planning Pinnacle plans were transferred in DICOM export protocols through the MOSAIQ system to the linear accelerator. Continuous gantry motion, dose-rate variation, and multi-leaf collimator (MLC) motion were approximated by optimizing individual beams at 4° gantry angle increments with MLC leaf positions varying by up to 4.6 mm for every 1° of gantry rotation.

Example 2

Plan Studies for Pancreatic Cancer Patients, VMAT Delivery and Dose Verification The original VMAT plans of five pancreatic cancer patients, with passive abdominal compression for respiratory control, were archived from the Pinnacle planning system, and were modified with the split short arcs of less than 30 seconds each. The modified short-arc VMAT plans were recalculated with the reassigned MUs of the short arcs for the summated doses. All patients were planned with 10-MV photon beams in the supine position. The minimum doses prescribed to the gross tumor volume (GTV), clinical target volume (CTV), and 95% planning target volume (PTV) were 55 Gy, 45 Gy, and 45 Gy in 25 fractions, respectively.

The original long-arc and modified short-arc VMAT plans were delivered by an Elekta Synergy® linear accelerator. Elekta VMAT delivery was basically by MU-based servo control. The accelerator used automatic dose-rate selection, which ensures that the maximal possible dose rate was chosen for each individual segment of the arc. The possible dose rates were 440, 222, 112, and 57 MU/min. The delivery time of each long arc/short arc was recorded from the MOSAIQ system.

One patient had original VMAT plans with 3 arcs, three with 2 arcs, and one with 1 arc. The median and mean (±standard deviation) delivery times of each arc in the original VMAT plans were 122.5 seconds and 123.7±21.5 seconds, with a range from 95 to 168 seconds. After the programmed segmentation of long arcs, one patient had modified VMAT plans with 24 short arcs, three with 16 short arcs, and one with 8 short arcs. The median and mean delivery times of each short arc in the modified VMAT plans were 20.0 seconds and 20.1±3.6 seconds, with a range from 13 to 30 seconds (Table 1).

Doses were verified using the MapCHECK 2 device version 5.02.00.02 (Sun Nuclear Corporation, Melbourne, Fla., USA). The differences between the planned and measured doses were analyzed by gamma tests for the original long-arc plans. Besides, gamma tests were taken for the differences between the planned doses of the original long-arc plans and the measured doses of the modified short-arc plans. The criteria of gamma evaluation were 3% dose difference and 3-mm distance to agreement. Γ≤1 was defined as the verification passing the criteria and satisfying at least 95% of points.

The recalculated dose-volume data with the summation of segmented short arcs showed negligible difference from the original VMAT plans. The average dose differences in minimum dose between the original and modified plans for GTV (55 Gy), CTV (45 Gy), and 95% PTV (45 Gy) were 1.3±0.8 cGy, 3.0±4.6 cGy, and 1.4±1.5 cGy, respectively. The dose-volume histogram for targets and organs at risk of a representative patient is shown in FIG. 1B.

The average passing rates of 3%/3-mm gamma index for accuracy of dose delivery were not different, 99.1%±1.6% for the original VMAT plans, and 98.8%±2.1% for the modified VMAT plans (p=0.24 by paired Student t test). The 2-dimensional dose verifications on the MapCHECK 2 device of a representative patient's original and modified VMAT plans were shown in FIG. 1C.

What is claimed is:

1. A programmable method for setting subarcs in a segmented short-arc volumetric modulated arc therapy (VMAT) to fit a breath-hold interval, comprising the following steps:
   (a) dividing an arc in the VMAT into a certain number of subarcs;
   (b) setting four cut-edge control points within each subarc to form three segments, each segment defining a range over which a prescribed dose of radiation is delivered with the segments arranged in a continuous manner on the subarc and the delivery of the prescribed radiation dose being continuous through the segments;
   (c) setting monitor units (MUs) for the segments within each subarc, wherein the monitor units for a starting (first) control point, second control point, third control point and stopping (fourth) control point are designated as $MU_1$, $MU_2$, $MU_3$ and $MU_4$, respectively, and the stopping control point is a starting point of a subsequent subarc; and

TABLE 1

The number and delivery time (mean ± standard deviation) of arcs from the original and modified volumetric modulated arc therapy (VMAT) plans in five pancreatic cancer patients, and the quality assurance as gamma indexes of VMAT delivery

| | | Original VMAT plan | | | Modified short-arc VMAT plan | | |
|---|---|---|---|---|---|---|---|
| Patient no. | Arc number (Gantry angles) | Delivery time for each arc in seconds (total) | 3%/3-mm Gamma index (%) | 2%/2-mm Gamma index (%) | Arc number | Mean delivery time per arc in seconds (total) | 3%/3-mm Gamma index (%) | 2%/2-mm Gamma index (%) |
| 1 | 2 (270°-180°; 180°-270°) | 123, 122 (245) | 100.0 | 98.1 | 16 | 19.9 ± 2.0 (319) | 100.0 | 97.9 |
| 2 | 1 (181°-180°) | 111 (111) | 100.0 | 97.8 | 8 | 18.1 ± 2.3 (145) | 100.0 | 97.4 |
| 3 | 2 (200°-160°; 160°-200°) | 168, 145 (313) | 96.2 | 90.4 | 16 | 24.9 ± 2.9 (398) | 95.2 | 88.2 |
| 4 | 2 (300°-180°; 180°-300°) | 113, 110 (223) | 100.0 | 97.9 | 16 | 17.5 ± 2.5 (280) | 99.8 | 91.7 |
| 5 | 3 (270°-180°; 181°-179°; 180°-270°) | 130, 130, 95 (355) | 99.3 | 96.9 | 24 | 19.3 ± 2.8 (464) | 99.2 | 92.7 |

(d) determining a dose distribution within each subarc by setting delivered MUs in each segment, wherein the delivered MUs in a first segment are distributed according to a formula: $MU_1+X_2MU_2$; the delivered MUs in a second segment are distributed according to a formula: $(1-X_2)MU_2+X_3MU_3$; and the delivered MUs in a third segment are distributed according to a formula: $(1-X_3)MU_3+X_{4s}MU_4$; $X_2$ is a proportion of the delivered MUs distributed for the first segment between the starting control point and the second control point, while $(1-X_2)$ is a proportion of the delivered MUs distributed for the second segment between the second control point and the third control point; $X_3$ is a proportion of the delivered MUs distributed for the second segment between the second control point and the third control point, while $(1-X_3)$ is a proportion of the delivered MUs distributed for the third segment between the third control point and the fourth (stopping) control point; and $X_{4s}$ is a proportion for converting the delivered MUs at the stopping control point to that at the starting control point of the subsequent subarc;

wherein each subarc is in an interval less than a single breath-hold.

2. The method of claim 1, wherein the $MU_1$ of the first (starting) segment is 0 and $X_{4s}$ is 1.

3. The method of claim 1, which is used in any of VMAT plans.

4. The method of claim 1, wherein each subarc takes a time less than 40 seconds.

5. The method of claim 1, wherein each subarc takes a time less than 30 seconds, 20 seconds or 15 seconds.

6. The method of claim 1, wherein each subarc takes a time 15 to 40 seconds.

7. The method of claim 1, wherein each subarc takes a time 15 to 30 seconds or 20 to 30 seconds.

8. A system setting split short arcs in a programmably segmented short-arc volumetric modulated arc therapy (VMAT) to fit a breath-hold interval, which comprises:

a unit for dividing an arc in the VMAT into a certain number of subarcs;

a unit for setting four cut-edge control points within each subarc to form three segments, each segment defining a range over which a prescribed dose of radiation is delivered with the segments arranged in a continuous manner on the subarc and the delivery of the prescribed radiation dose being continuous through the segments;

a unit for setting monitor units (MUs) for the segments within each subarc, wherein the monitor units for a starting control point, second control point, third control point and stopping control point are designated as $MU_1$, $MU_2$, $MU_3$ and $MU_4$, respectively, and the stopping control point is a starting point of a subsequent subarc; and a unit for determining a dose distribution within each subarc by setting delivered MUs in each segment, wherein the delivered MUs in a first segment are distributed according to a formula: $MU_1+X_2MU_2$; the delivered MUs in a second segment are distributed according to a formula: $(1-X_2)MU_2+X_3MU_3$; and the delivered MUs in a third segment are distributed according to a formula: $(1-X_3)MU_3+X_{4s}MU_4$, $X_2$ is a proportion of the delivered MUs distributed for the first segment between the starting control point and the second control point, while $(1-X_2)$ is a proportion of the delivered MUs distributed for the second segment between the second control and the third control point;

$X_3$ is a proportion of the delivered MUs distributed for the second segment between the second control point and the third control point, while $(1-X_3)$ is a proportion of the delivered MUs distributed for the third segment between the third control point and the stopping control point; and $X_{4s}$ is a proportion for converting the delivered MUs at the stopping control point to that at the starting control point of the subsequent subarc;

wherein each subarc is in an interval less than a single breath-hold.

9. The system of claim 8, wherein the $MU_1$ of the first (starting) segment is 0 and $X_{4s}$ is 1.

10. The system of claim 8, which is used in any of VMAT plans.

11. The system of claim 8, wherein each subarc takes a time less than 40 seconds.

12. The system of claim 8, wherein each subarc takes a time less than 30 seconds, 20 seconds or 15 seconds.

13. The system of claim 8, wherein each subarc takes a time 15 to 40 seconds.

14. The system of claim 8, wherein each subarc takes a time 15 to 30 seconds or 20 to 30 seconds.

* * * * *